US006455851B1

(12) United States Patent
Lord et al.

(10) Patent No.: US 6,455,851 B1
(45) Date of Patent: Sep. 24, 2002

(54) SPECTROSCOPIC REMOTE SENSING EXHAUST EMISSION MONITORING SYSTEM

(75) Inventors: Harry C. Lord; Marc M. Baum, both of Pasadena, CA (US)

(73) Assignee: Air Instruments and Measurement, Inc., Pasadena, CA (US)

( * ) Notice: Subject to any disclaimer, the term of this patent is extended or adjusted under 35 U.S.C. 154(b) by 0 days.

(21) Appl. No.: 09/547,154

(22) Filed: Apr. 11, 2000

Related U.S. Application Data

(63) Continuation-in-part of application No. 09/536,538, filed on Mar. 28, 2000, now abandoned.

(51) Int. Cl.[7] .................. G01N 21/00; G01N 21/17
(52) U.S. Cl. ...................... 250/338.5; 250/339.13; 250/343; 250/365; 250/504 R
(58) Field of Search ................... 250/338.5, 339.13, 250/343, 365, 504 R

(56) References Cited

U.S. PATENT DOCUMENTS 5,498,872 A * 3/1996 Stedman et al. ......... 250/338.5
5,807,750 A * 9/1998 Baum et al. ................ 436/164

\* cited by examiner

Primary Examiner—Bruce Anderson
Assistant Examiner—Nikita Wells
(74) Attorney, Agent, or Firm—David O'Reilly

(57) ABSTRACT

A spectroscopic IR and UV-vis absorption remote exhaust emission monitoring system and sensing instrument for non-invasive, multicomponent analysis of the exhaust plume emitted by in-use vehicles. The concentration of CO, $CO_2$, HC, NO, $N_2O$, $C_2H_2$, $NH_3$, $SO_2$, Aromatic hydrocarbons, aldehydes, HONO, $NO_2$, and dust, among others and in any combination there-of, in such a mixture can be determined in real-time, or via post-processing of stored spectral data. The sensor employs an IR and a UV-vis sources, and the physically offset, collimated beams traverse the probed air column, typically a roadway, a plurality of times, before returning to the instrument. Although the IR and UV-vis beams converge at the optics opposite the instrument, they are not coaxial and, thus, do not require an optical device (i.e., dichroic beam splitter) to separate them. The separate IR and UV-vis beams are focused on the slits of rapid spectrometers, where they are analyzed to yield wavelength-resolved spectra (i.e., graphs of digital signal intensity versus radiation wavelength). These spectrometers can either be rapid scanning dispersive devices, dispersive devices employing linear or two-dimensional detector arrays, or Fourier transform spectrometers. The graphs are converted into absorbance spectra and are subsequently processed with pattern recognition algorithms and a spectral reference database to afford analyte concentration.

24 Claims, 10 Drawing Sheets

SPECTROSCOPIC REMOTE SENSING EXHAUST EMISSION MONITORING SYSTEM

CROSS-REFERENCE TO RELATED APPLICATIONS

This application is a continuation-in-part of applications' co-pending patent application Ser. No. 09/536,538, filed Mar. 28, 2000, which is now abandoned.

BACKGROUND OF THE INVENTION

1. Field of the Invention

This invention relates to an exhaust emission monitoring system and more particularly relates to a spectroscopic absorption remote sensing instrument for multi-component analysis of exhaust plumes emitted by in-use vehicles.

2. Background Information

Emissions from mobile sources are well known to play a central role in urban air pollution (photochemical smog formation, violation of carbon monoxide (CO) and ozone ($O_3$) standards, and aerosol formation). In 1994, the U.S. Environmental Protection Agency (US EPA) estimated that, for the previous year, U.S. on-road vehicles contributed 62%, 32%, and 26% of all CO, nitrogen oxide ($NO_x$), and volatile organic compound emissions, respectively. ("National Air Pollution Trends, 1900–1993," United States Environmental Protection Agency, Office of Air Quality Planning & Standards, 1994).

It is well known that numerous chemical species can be monitored non-invasively in ambient air with a high degree of precision ("Air Monitoring by Spectroscopic Techniques", Ed. Sigrist, M. W., John Wiley & Sons, New York). Remote sensing of exhaust from light duty motor vehicles has provided a wealth of useful information with respect to CO and total hydrocarbon (HC) emissions. Data collected from these investigations indicate that approximately half of CO and HC emissions from in-use vehicles are generated by less than 10% of the fleet.

Over the past 3 years NO emissions have been reported to follow similar trends. Moreover, remote sensing data suggests that fleet dynamometer testing significantly underestimates tailpipe emissions, and contributes to errors in model predictions (e.g., U.S. EPA's MOBILE4). A knowledge of the chemical composition of the exhaust plume emitted by on-road vehicles on a car-by-car basis therefore is essential when developing effective pollution abatement strategies.

Most existing remote sensing studies have relied on non-dispersive infrared (NDIR) and non-dispersive ultraviolet (NDUV) spectroscopy. This research resulted in several patented inventions (C. V. Swanson, Jr., U.S. Pat. No. 4,924,095, issued May 8, 1990; G. Bishop & D. H. Stedman, U.S. Pat. No. 5,210,702, issued May 11, 1993; L. H. Rubin & M. D. Jack, U.S. Pat. No. 5,418,366, issued May 23, 1995; M. D. Jack, U.S. Pat. No. 5,591,975, issued Jan. 7, 1997; M. D. Jack et al, U.S. Pat. No. 5,831,267, issued Nov. 3, 1998). They are based on NDIR analyzers that rely on a plurality of detectors, one for each monitored gas as well as one reference detector, to make their measurements. In one case (Bishop et al.) an NDUV channel is added to measure NO. They share similar optical designs, such as a rotating polygonal mirror to channel the unfiltered radiation sequentially to each detector, and use narrow bandpass optical filers to isolate the spectral window that matches the absorption feature of the gas of interest.

Optical designs for the remote sensing of vehicle exhaust have also been patented separately (M. E. Sullivan et al, U.S. Pat. No. 5,563,420, issued Oct. 8, 1996; J. Didomenico et al, U.S. Pat. No. 5,644,133, issued Jul. 1, 1997). While these analytical techniques provide excellent data for CO and $CO_2$, accurate HC data has been difficult to acquire due to modest sensitivity, typically 500 parts per million (ppm, 1 ppm=1 part in $10^6$ by volume or moles) detection limit ($3\sigma$), and water interference. The sensitivity to NO is even poorer (300 ppm precision, $1\sigma$), limiting the instrument to the identification of gross polluters or fleet evaluations.

Bishop et al. later enhanced their invention by replacing the NDUV channel with a dispersive spectrometer using a photodiode array detector (G. Bishop et al, U.S. Pat. No. 5,401,967, issued Mar. 28, 1995; G. Bishop et al, U.S. Pat. No. 5,498,872, issued Mar. 12, 1996). However, the first reported use of a dispersive spectrometer using an array detector to remotely monitor the NO UV band in vehicle exhaust dates back to 1984. (Pitts, J. N.; Biermann, H. W.; Winer, A. M.; Tuazon, E. C. Atmos. Environ. 1984, 18, 847–854).

More recently, tunable infrared diode laser absorption (TIDLA) spectrometers have been utilized in a remote sensing configuration to measure NO in vehicle exhaust with greater sensitivity and selectivity. More patents have resulted from these inventions (D. D. Nelson et al, U.S. Pat. No. 5,877,862, issued Mar. 2, 1999). Unfortunately, these TDLA spectrometers are impractical for field use as they require cryogenic cooling to operate in the mid-IR (where most of the strong bands are located). They also need skilled operators and can be prohibitively expensive for multi-component applications. Fourier transform infrared (FTIR) spectrometers have become very popular for open path monitoring, but have found limited application in the remote sensing of auto exhaust. This is partially due to low signal-to-noise ratios from the short averaging times (0.5–1.0s). Additionally, such systems are often too delicate for field use; sturdier and faster spectrometers are available, but can be expensive.

A rugged, low-cost alternative to existing remote sensors is needed to measure criteria pollutants (CO, HC, NO), as well as $CO_2$, with equal or increased precision. The instrument should also be capable of measuring other compounds of importance to tropospheric photochemistry. For instance, formaldehyde (HCHO) and acetaldehyde ($CH_3CHO$) are key to the photolytic generation of hydroperoxyl and acylperoxy radicals; nitrous acid (HONO) is an important source of hydroxyl radicals; nitrogen dioxide ($NO_2$) affords ozone upon photolysis and reacts with hydroxyl radicals to yield nitric acid; aromatic hydrocarbons (e.g., benzene, toluene, xylene) are important reaction sinks for hydroxyl radicals, often affording secondary organic aerosols. Ammonia ($NH_3$) is known to be emitted by vehicles equipped with three-way catalysts operating under fuel-rich conditions. $NH_3$ emissions play a key role in the production of fine particulate matter. Finally, a useful remote sensor should store sufficient spectral information in the "snapshot" of the exhaust plume to enable quantification of "unknown species" at a later date.

These challenges can be met with the disclosed invention by using a novel optical design to allow dispersive IR and UV-vis spectroscopy in combination with powerful chemometric techniques.

BRIEF DESCRIPTION OF THE INVENTION

The principal purpose of the disclosed invention consists in the quantitative analysis of gas-phase components and particulates in the exhaust plume emitted by moving vehicles. This measurement is made non-invasively by using novel remote sensing technology.

The present invention is unique in its optical design and by virtue of the fact that dispersive IR and UV-vis spectrometers are used to make the measurements. The use of wavelength-resolved data both in the IR and UV-vis has not been reported previously to make remote measurements of pollutant levels in the exhaust plume of in-use vehicles.

The instrument is capable of measuring numerous pollutants emitted by in-use vehicles, including, but not limited to, CO, $CO_2$, HC (as propane), NO, and dust.

The instrument has the capability of measuring numerous other pollutants, such as $NH_3$, sulfur dioxide ($SO_2$), $CH_3CHO$, HONO, $NO_2$, $N_2O$, toluene, benzene, xylene, benzaldehyde. Addition of these measurement channels does not necessitate any hardware modifications and only requires minor adjustment to the analyzer software configuration file.

The analyzer is able to achieve the above measurements by using a pair of collimated infrared (IR) and ultraviolet (UV) beams emitted at right angles across a roadway. There, the beams are collected by an optical device, such as a spherical mirror, and returned to the analyzer. Thus, two, or multiples of two (i.e., 2, 4, 6, 8, etc.), optical passes are made across the roadway traveled by moving vehicles. The radiation is analyzed by one or more dispersive UV and one or more dispersive IR spectrometers.

The UV and IR spectrometers generate spectra at high frequencies (e.g., 100 Hz) and these spectra span a wide spectral window (e.g., 200 nm in the UV and 2000 $cm^{-1}$ in the IR). Characteristic absorption signatures of numerous gases occur in these spectral windows, such as CO, $CO_2$, and aliphatic HC (as propane) in the IR, and NO in the UV, and dust scattering in the visible. One or more pattern recognition algorithms match a spectral database, containing reference spectra of the gases of interest, to the spectra of the vehicle exhaust and, herewith, calculate the concentration of the analytes of interest in the exhaust plume.

The concentrations of the analytes of interest are output to a storage device in the analyzer and to a data acquisition system by means of a standard digital data communication protocols (e.g., RS-232). A set of electronic triggers also are output with the data to validate the measurement, and indicate pass/fail status of the vehicle with respect to pollution emission regulations or standards.

The above and other objects, advantages, and novel features of the invention will be more fully understood from the following detailed description and the accompanying drawings, in which:

DETAILED DESCRIPTION OF THE INVENTION

The accompanying figures illustrate complete preferred embodiments of the present invention and the best modes presently devised for the practical application of the principles thereof.

Figure 1:
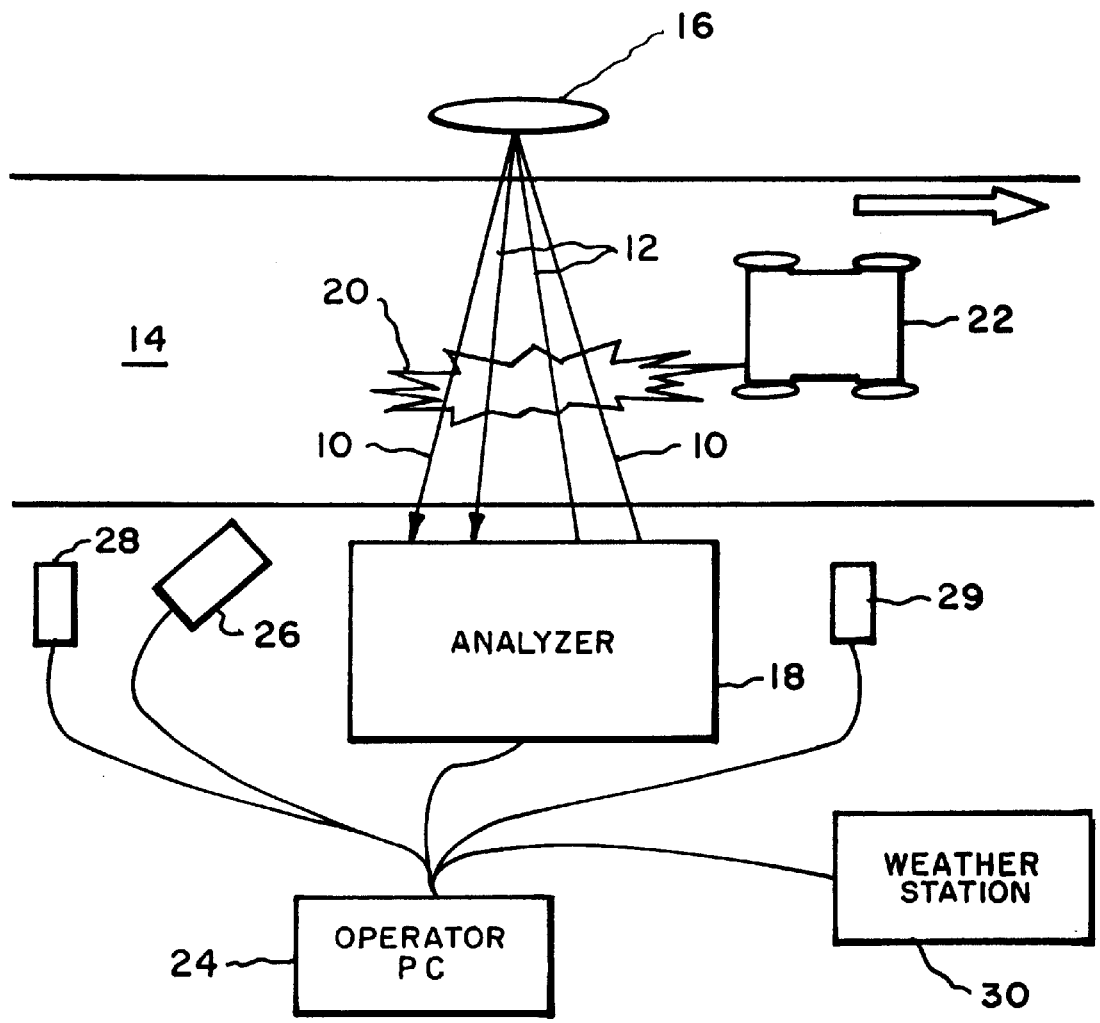
FIG. 1 is a detailed block diagram of a remote vehicle exhaust monitoring system constructed according to the invention.

Briefly in the preferred embodiment of FIG. 1 a collimated beam of IR radiation 10 and a physically offset beam of collimated UV radiation 12 from analyzer 18 are sent across monitored roadway 14. The radiation converges at a suitable optical device, such as return mirror 16 and is reflected back to analyzer 18, where it is detected and processed to yield the concentration of the measured gases emitted in exhaust plume 20 of moving vehicle 22. The concentration data is sent to an operator PC 24. Video camera 26 simultaneously sends an image of the vehicle's license plate to the operator PC. Speed/acceleration information on vehicle 22 is acquired with suitable devices 28, 29 such as an Image Sensor Package from Autoscope of Anaheim, Calif. and also transmitted to the operator PC. Weather station 30 such as a Model 110-WS-14 Weather Station from Novalynx of Grass Valley, Calif. also sends its data e.g., wind speed and direction, ambient temperature, pressure, and light levels) to the operator PC. The operator PC displays, tags, and stores the data for each measured vehicle.

The following describes the preferred embodiment in greater detail. In FIG. 1 collimated IR beam 10, and adjacent, collimated UV beam 12 are projected across roadway 14 and converge at return mirror 16. The center-center distance between the two beams at analyzer 18 are kept to a minimum; a separation of 5–15 cm is optimal. Return mirror 16 is a spherical mirror, 15–30 cm in diameter, with a focal length of 2 m, or greater. In another preferred embodiment of the invention, return mirror 16 consists of a spherical mirror with variable and adjustable focal length (e.g., between 2.5 and 8 m), such as part number RR12 supplied by InfraRed Analysis (Anaheim, Calif.). Collimated IR and UV beams 10, 12 are focussed onto optical receiving ports in analyzer 18 that are distributed symmetrically with respect to the corresponding projection ports. The returned broadband radiation is detected in analyzer 18 as described in greater detail hereinafter.

Optical probes of IR and UV radiation 10, 12 are used to remotely detect the concentration of multiple gaseous and particle components of the exhaust plume 20 emitted by moving vehicle 22. These concentrations are calculated on the basis that said gaseous pollutants absorb IR and UV-vis radiation of a specific wavelength. The amount of absorbed radiation is proportional to the gas concentration. Particles scatter radiation in a manner that can be related to their concentration. These measurements are output in digital or analog form from analyzer 18 to operator PC 24, where they are stored and displayed. Video camera 26 captures a digital image of the license plate of vehicle 22 and, when triggered by analyzer 18, sends the image to operator PC 24 so it can be stored with the corresponding concentration measurements. Speed and acceleration measurement devices 28, 29 and weather station 30 send their readings to operator PC 24 in a similar fashion.

Figure 2:
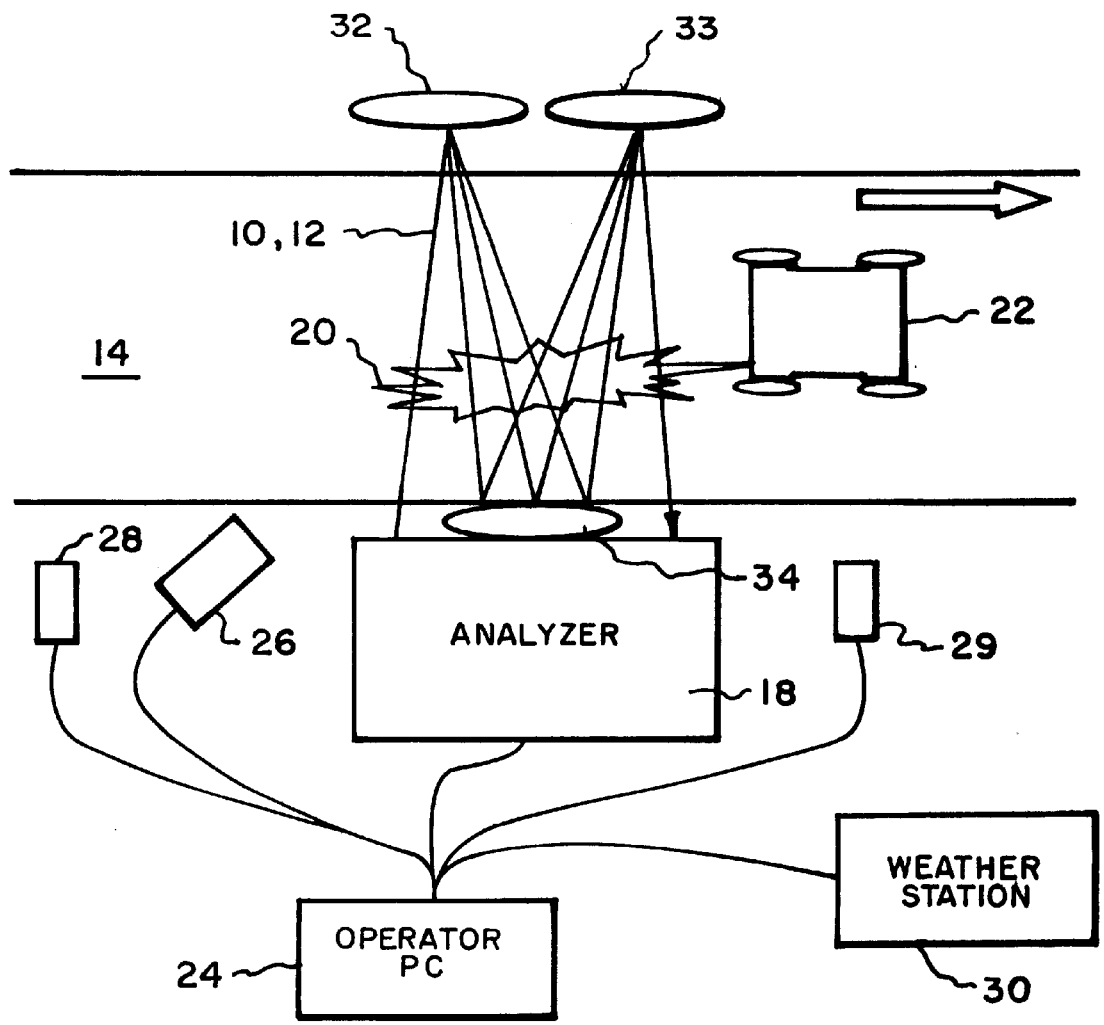
FIG. 2 is a detailed block diagram of a second embodiment of the remote vehicle exhaust monitoring system of FIG. 1.

The embodiment of FIG. 2 is analogous to the one shown in FIG. 1, except that the offset UV and IR beams (shown as one beam for the sake of clarity) traverse the roadway 14 two or more times. An array of two spherical mirrors 32, 33 direct the beams back to spherical mirror 34. This allows a plurality of optical passes (i.e., two or more) to be achieved.

This alternate arrangement shows each adjacent UV and IR beams (shown as one beam in FIG. 2 for the sake of clarity) traversing roadway 14 a plurality of times (typically eight), exceeding the two passes shown in FIG. 1. One preferred embodiment of the optical system is loosely based on the popular design pioneered by White (White, J. U. J. Opt. Soc. Am. 1942, 32, 285–288) and uses a pair of adjacent spherical mirrors 32, 33 across from analyzer 18 and another spherical mirror 34 mounted on the analyzer. Such an optical system allows more of exhaust plume 20 to be optically probed and results in greater sensitivity than the double pass arrangement shown in FIG. 1. The high volume of the optical envelope also affords excellent overlap with exhaust plume 20 further improving measurement sensitivity.

Figure 3:
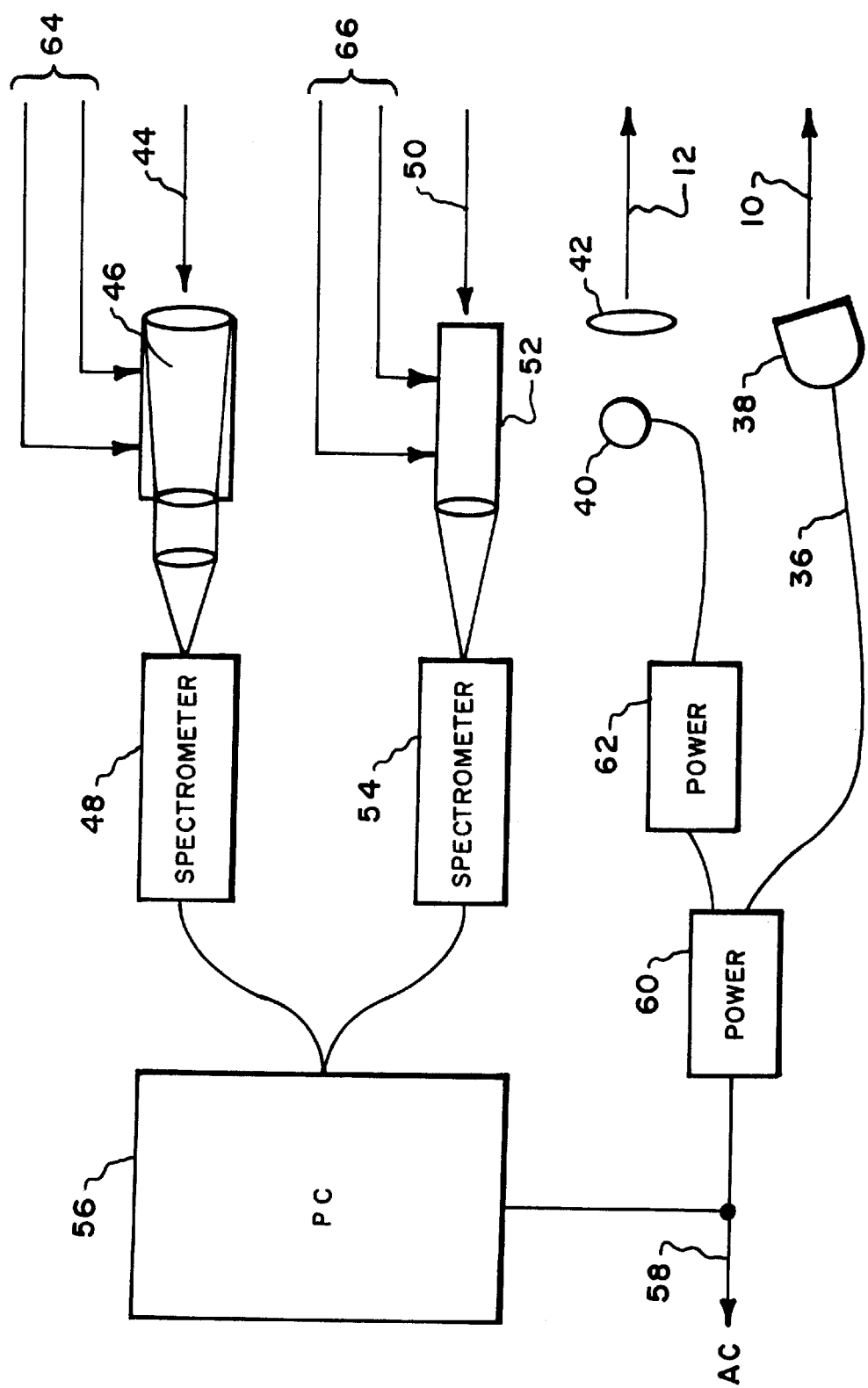
FIG. 3 is a detailed block diagram of one embodiment of an optical system for an analyzer used in the remote vehicle exhaust monitoring system according to FIGS. 1 and 2.

One embodiment of the optical design for the analyzer is shown in FIG. 3; it is compatible with the system layout shown in FIGS. 1 and 2. Radiation from IR source 36 is collected by optical device 38, collimated at 10, and projected across the roadway. Radiation from UV emitter 40 is collected by optical device 42, collimated at 12, and projected across the roadway. Return IR radiation 44 is collected by optical assembly 46 and focussed onto the slit of dispersive spectrometer 48. Similarly the corresponding UV radiation 50 is collected by optical assembly 52 and focussed onto the slit of dispersive spectrometer 54. Signals from both spectrometers are sent to analyzer PC 56 where they are processed. The unit is powered by mains AC 58 and each radiative source is powered by corresponding power supplies 60 and 62. Gas lines 64 and 66 are connected to optical assemblies 46 and 52, which also act as inline calibration cells. In FIG. 3, source 36 is an emitter of IR radiation, such as a silicon carbide rod heated to 1000 degrees C., which is located at the focus of parabolic mirror 38. This optical device collimates the IR beam and projects collimated beam 10 across the roadway. A plano convex lens or other suitable optical device can be used in lieu of paraboloid 38 to achieve collimation. UV source 40, such as emitted by a deuterium arc source or a high pressure xenon lamp, is collected by a fused silica plano convex lens 42, or other suitable collimating optic, and collimated. Collimated beam 12 is projected across the roadway so as to converge with IR beam 10 at the center of the mirror on the opposite side. Both IR and UV radiative sources are powered by stable power supplies 60 and 62 respectively.

Return IR beam 44 is collected by sealed optical assembly 46 and focussed onto the entrance slit of IR spectrometer 48. The optical assembly can consist of a three-lens (made of an IR transmitting material such as calcium fluoride or zinc selenide) telescope designed to maximize the collection of IR radiation and transmission through the slit of spectrometer 48. A simpler optical assembly consisting of a plano convex lens facing the spectrometer and a flat window at the opposite end can also be used, although with inferior results. Additionally, the lenses that seal the front and end of the telescope also mean that optical assembly 46 can be used as an in-line calibration cell. Calibration gases can be flown through the cell to routinely calibrate IR spectrometer 48 and validate the readings it produces. The signal from IR spectrometer 48 is digitized and processed in PC 56.

Return UV beam 50 is collected by sealed optical assembly 52 and projected onto the entrance slit of UV spectrometer 54. Optical assembly 52 can consist of a tube with a flat fused silica window at one end (further from spectrometer) and a plano convex lens at the other end. A more complex optical system consisting of a plurality of lenses can also be used. As with IR optical assembly 46, optical assembly 52 is also used as an in-line calibration cell to calibrate UV spectrometer 54 with certified cylinder gases. The signal from the UV spectrometer is transmitted to and processed in PC 56.

The signals from both spectrometers are accurately synchronized in PC 56. Note that PC 56 can be a desktop PC, an industrial PC, or a miniaturized PC bus, such as that employed in the PC-104 architecture.

All optical components, including windows, are made of materials and coatings that optimize the refraction and reflection of the radiation they are in contact with. For example, UV mirrors are coated with aluminum-magnesium fluoride-silica; this coating can also be used when UV and IR beams are reflected off a common mirror. IR lenses are usually made of zinc selenide or calcium fluoride. UV lenses are usually made of fused silica.

The different means of achieving wavelength-resolved spectral data in the Mid-IR (2–5.5 $\mu$m), using spectrometer 48 and in the UV-vis (190–800 nm), using spectrometer 54 are described hereinafter. Note that an analogous system can be used to obtain wavelength-resolved spectral data in the near-IR (0.8–2 $\mu$m) and in the far-IR (5.5–20 $\mu$m).

One type of the spectrometer suitable for use in this invention is the Monolight spectrum analysis system supplied by Macam Photometrics, Ltd. (Livingston, Scotland). In this device, a blazed diffraction grating (optimized to 4 $\mu$m for mid-IR measurements) is mounted to a synchronous DC motor. The revolution speed of the motor is 12.5 Hz, but can be faster or slower. Broadband IR radiation enters the device via a slit, reflects off an Ebert mirror and strikes the rotating grating. The dispersed (i.e., wavelength separated) radiation strikes the Ebert mirror a second time and exits the monochromator via a second slit. The monochromatic radiation then strikes a suitable detector, such as a photomultiplier tube or photodiode in the UV-vis, and a lead selenide or mercury cadmium telluride detector in the IR. Other analogous rapid scanning, robust devices would be considered equivalent.

The spectrometer of the preferred embodiment includes a linear array, consisting of a plurality, typically 128 or more, of detectors. Examples of suitable array detectors include Hamamatsu (Bridgewater, N.J.) 1024 element photodiode array and Sony Electronics Inc. (San Jose, Calif.) 2048 element CCD array for UV-vis measurements. For mid-IR measurements, pyroelectric and thermopile array systems, as supplied by Ion Optics, Inc. (Waltham, Mass.), multiplexed lead sulfide and lead selenide arrays Textron Systems (Petaluma, Calif.) and/or Litton Electro-Optical Systems (Tempe, Ariz.) and/or SensArray Corporation (Burlington, Mass.) would be suitable. Other detector arrays, such as mercury cadmium telluride, supplied by Cincinnati Electronics Corp. (Mason, Ohio), and indium antimonide, supplied by Litton Electro-Optical Systems (Tempe, Ariz.), could also be used for IR measurements.

The array is optically interfaced with a grating, such as a holographic grating, which disperses the broadband radiation into its component wavelengths without the need for moving mechanical parts. Commercial array spectrometers, such as Ocean Optics (Dunedin, Fla.) S-2000 UV-vis spectrometer, can also be used in a preferred embodiment of the present invention.

It should be noted that the use of dispersive IR spectroscopy to measure pollutants in vehicle exhaust emissions is not new. McIntosh et al. patented an extractive vehicle exhaust emissions analyzer in 1972 (L. D. McIntosh et al., U.S. Pat. No. 3,696,247, issued Oct. 3, 1972) using a concave grating optically interfaced to a plurality of exit slits, each accommodating one detector. Despite using dispersive optics, the system does not produce wavelength-resolved spectra, as no means for scanning the spectrum exists. The grating is merely a means for separating the broadband radiation into its component wavelength, and directing the radiation to a small number (typically 5) of detectors each measuring one gas, CO, $CO_2$, HC, and NO respectively. As with systems using narrow bandpass optical filters to isolate the spectral window of interest (e.g., Bishop et al.), a single voltage is generated for each measured gas (i.e., one-dimensional measurement). Additionally, the invention disclosed by McIntosh et al. is an extractive device, where a gas sample needs to be transferred from the vehicle exhaust into a sampling cell in the instrument where the measurement takes place. This is a completely different approach to the remote, non-invasive measurements in the present invention.

Another extractive sensor using dispersive optics to make measurements of vehicle exhaust emissions in the IR was described by Peters et al. (R. P. Peters et al., U.S. Pat. No. 5,550,375, issued Aug. 27, 1995). The sensor employs a single detector, has no means of wavelength scanning, and, thus, cannot produce wavelength-resolved spectra.

The present invention therefore includes a unique approach not known in the art. It combines IR and UV-vis spectroscopy, using a novel optical design, to allow the remote, non-invasive collection of two dimensional spectra, i.e., wavelength and intensity domains, of the exhaust plume emitted by moving or stationary vehicles.

Another preferred type of spectrometer is a FTIR and/or FTUV spectrometer that may be used as a means of obtaining wavelength-resolved spectral measurements. Remote sensors using FTIR spectrometers as a means of analyzing radiation have been described in the art (H. A. French, U.S. Pat. No. 4,676,642, issued Jun. 30, 1987; R. T. Kroutil et al., U.S. Pat. No. 5,061,854, issued Oct. 29, 1991). However, these devices were not used in conjunction with UV spectrometers in the optical configuration disclosed here, nor were they used to measure vehicle exhaust emissions. Note that most FTIR spectrometers do not have a sufficiently high signal-to-noise ratio in a ≈100 msec. measurement window to be of use in the application.

All spectrometers should have a duty cycle under 10 Hz, with a 100 Hz duty cycle being more desirable. Spectral data needs to have a signal-to-noise ratio sufficiently large to allow analytes of interest to be measured in 500 msec. range or less of data collection.

Yet another variation of the present invention uses a 2D-array with a plurality of detector pixels (at least 16×16), responsive to UV-vis and/or IR radiation, to image a section of the emitted exhaust plume (e.g., NO column density in a two-dimensional cross-section of the plume).

Figure 4:
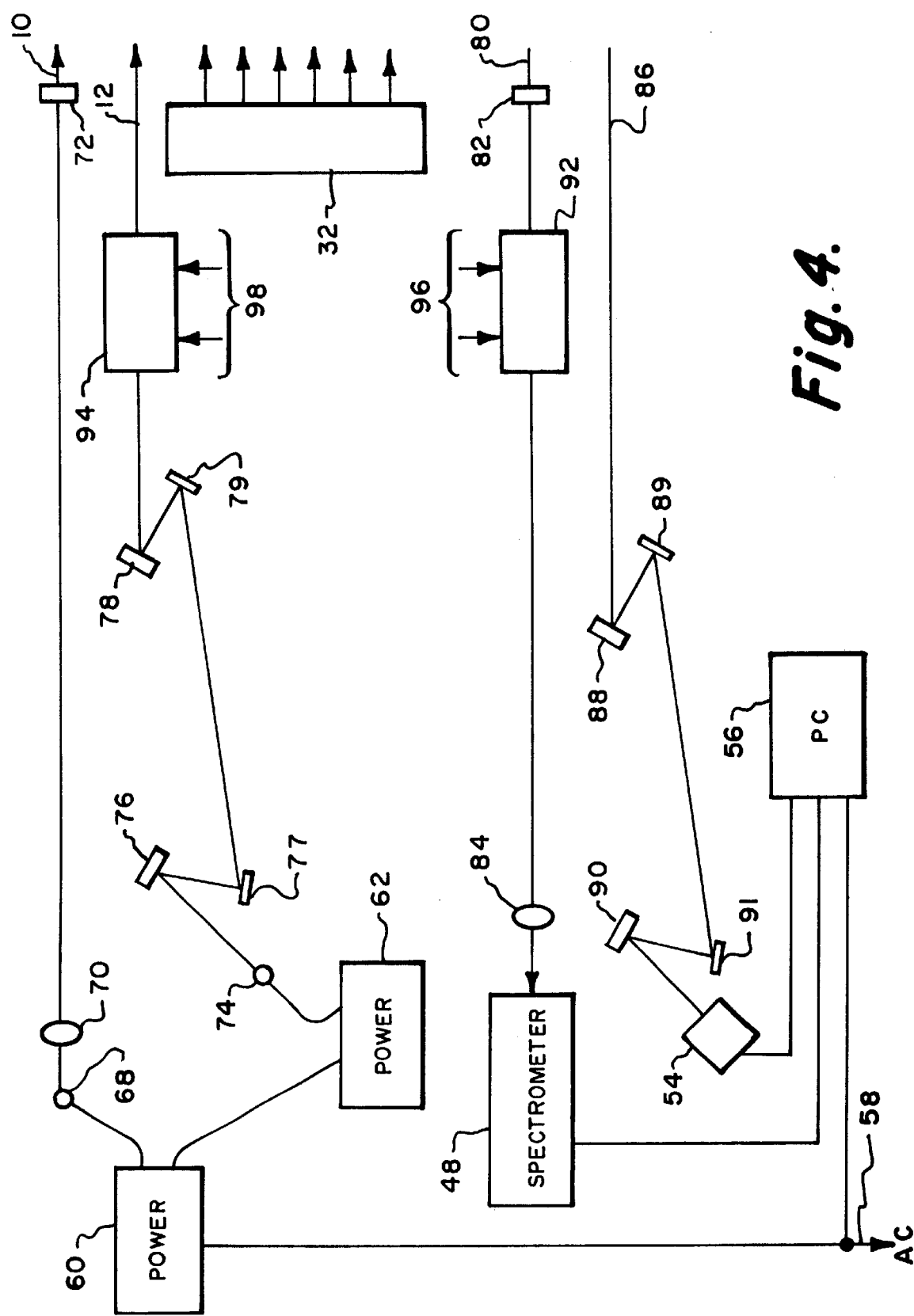
FIG. 4 is another block diagram of an optical arrangement for the analyzer of the remote vehicle exhaust emission monitoring system according to the invention.

FIG. 4 illustrates another embodiment of the optical design for the analyzer that is also compatible with the layout shown in FIGS. 1 and 2. Radiation from IR source 68 is collected by optical devices 70 and 72, collimated 10, and projected across the roadway. Radiation from UV emitter 74 is collected by optical devices 76 through 79, collimated 12, and projected across the roadway. The return IR radiation 80 is collected by optical devices 82 and 84 and focussed onto the slit of dispersive spectrometer 48.

Similarly, the corresponding UV radiation 86 is collected by optical devices 88 through 91 and focussed onto the slit of dispersive spectrometer 54. Signals from both spectrometers are sent to analyzer PC 56 where they are processed. The unit is powered by mains AC 58 and each radiative source is powered by corresponding power supplies 60 and 62. In-line calibration cells 92 and 94 are connected to gas lines 96 and 98 respectively.

FIG. 4 is an alternative embodiment of the remote sensor. The primary difference compared with FIG. 3 is the optical design. Radiation from a broadband IR emitter is collected and collimated by plano convex lens 70 and corrected by field lens 72 before collimated beam 10 is projected across the roadway. Return IR beam 80 is refracted by field lens 82 onto plano convex lens 84 that focuses the IR radiation on the entrance slit of IR spectrometer 48.

A pair of Schwarzshield telescopes comprised of concave and convex mirrors 76, 78 and 77, 79 respectively are used to collect the UV radiation emitted by emitter 74 and project collimated beam 12 across the roadway. Return UV beam 86 is collected by another pair of Schwarzshield telescopes 88, 89 and 90, 91 and focused onto the entrance slit of UV spectrometer 54. Both spectrometers fit the above description and are connected to analyzer PC 56, as in FIG. 3., Note that field mirror 32 is shown to illustrate how this optical design can be used in a multipass configuration.

In-line calibration cells 92 and 94 are used to periodically verify the response of the analyzer. IR 96 and UV-absorbing 98 cylinder calibration gases to be flown through these devices, which are made of anodized aluminum, stainless steel, or glass bodies, with sealed inert windows that transmit radiation in the range measured by the corresponding spectrometer.

Figure 5:
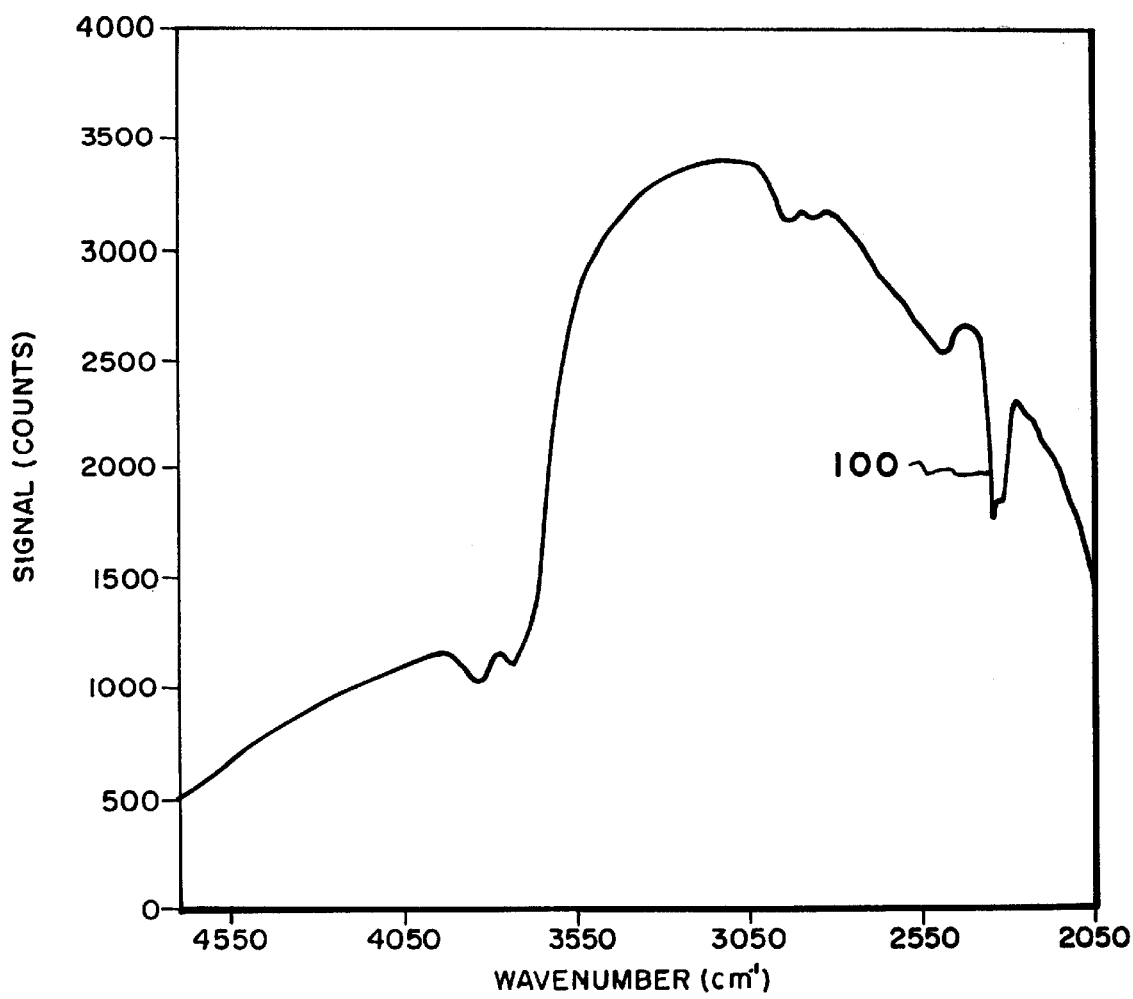
FIG. 5 is a graph illustrating the Mid-IR spectrum of ambient air using the IR spectrometer.

FIG. 5 is a graph of the Mid-IR spectrum of ambient air using the IR spectrometer. The spectrum is indicative of the spectrometer's wide spectral bandwidth and of its optical resolution, as evidenced by feature 100 corresponding to an absorption by ambient $CO_2$.

A typical Mid-IR spectrum obtained with the IR spectrometer is shown. The spectrum shape is the result of the optical properties of the materials the light is in contact with as well as the emissive properties of the IR source and the response of the lead selenide detector. Dip 100 in the spectrum is the result of $CO_2$ absorption, due to the presence of ambient $CO_2$ in the path of the beam. FIG. 5 is illustrative, to one versed in the art, of the spectral range and resolution of the IR spectrometer.

Figure 6:
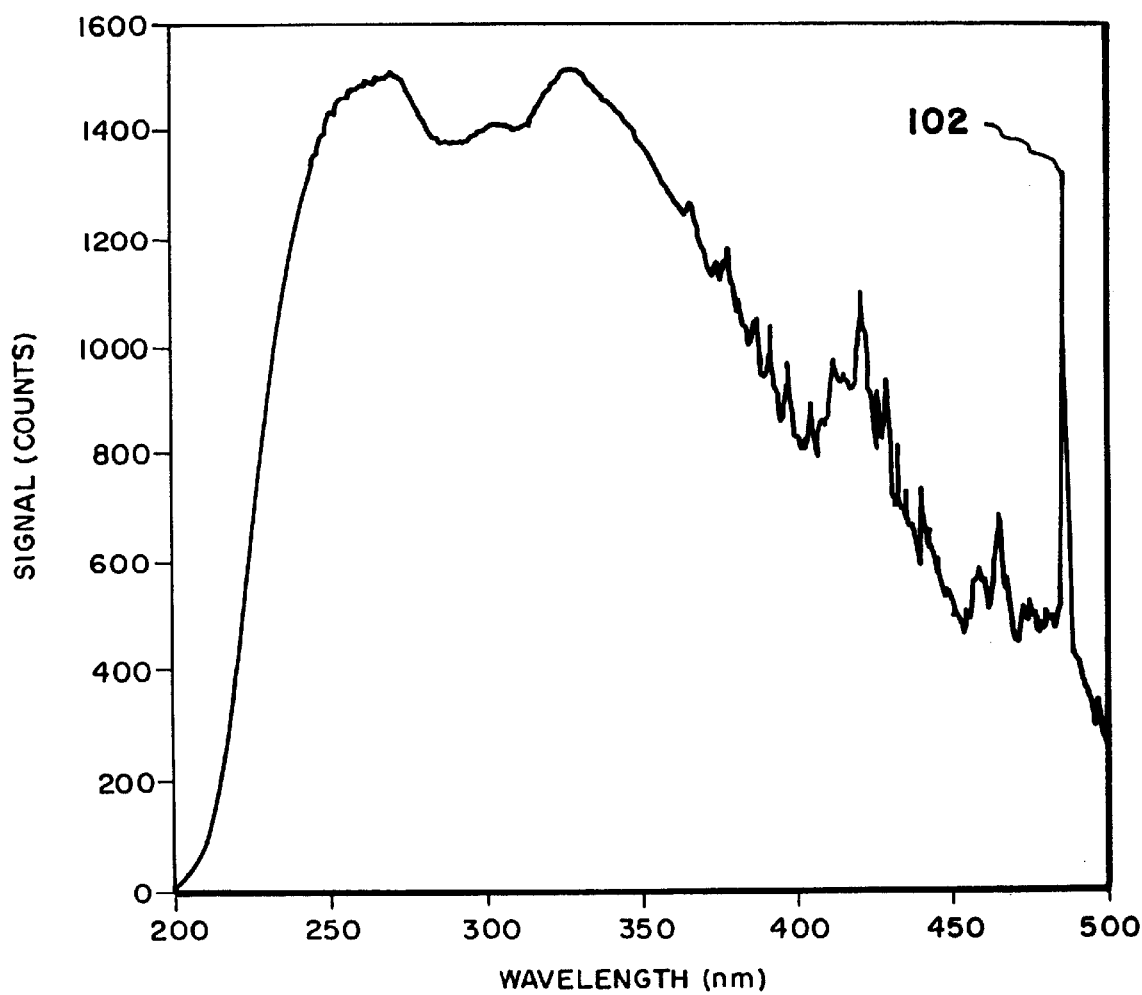
FIG. 6 is a graph illustrating the UV-vis spectrum of ambient air using the UV spectrometer.

FIG. 6 is a graph of the UV-vis spectrum of ambient air using the UV spectrometer. The spectrum is indicative of the spectrometer's wide spectral bandwidth and of its optical resolution, as evidenced by feature 102 corresponding to an emission band from the deuterium arc.

A typical UV-vis spectrum obtained with the UV spectrometer is shown. The spectrum shape is the result of the optical properties of the materials the light is in contact with as well as the emissive properties of the UV source and the response of the silicon detectors in the linear CCD array. A sharp peak indicated at 102 is a characteristic emission line of deuterium, the gas used in the corresponding arc lamp. Again, FIG. 6 is illustrative, to one versed in the art, of the spectral range and resolution of the UV-vis spectrometer.

Figure 7:
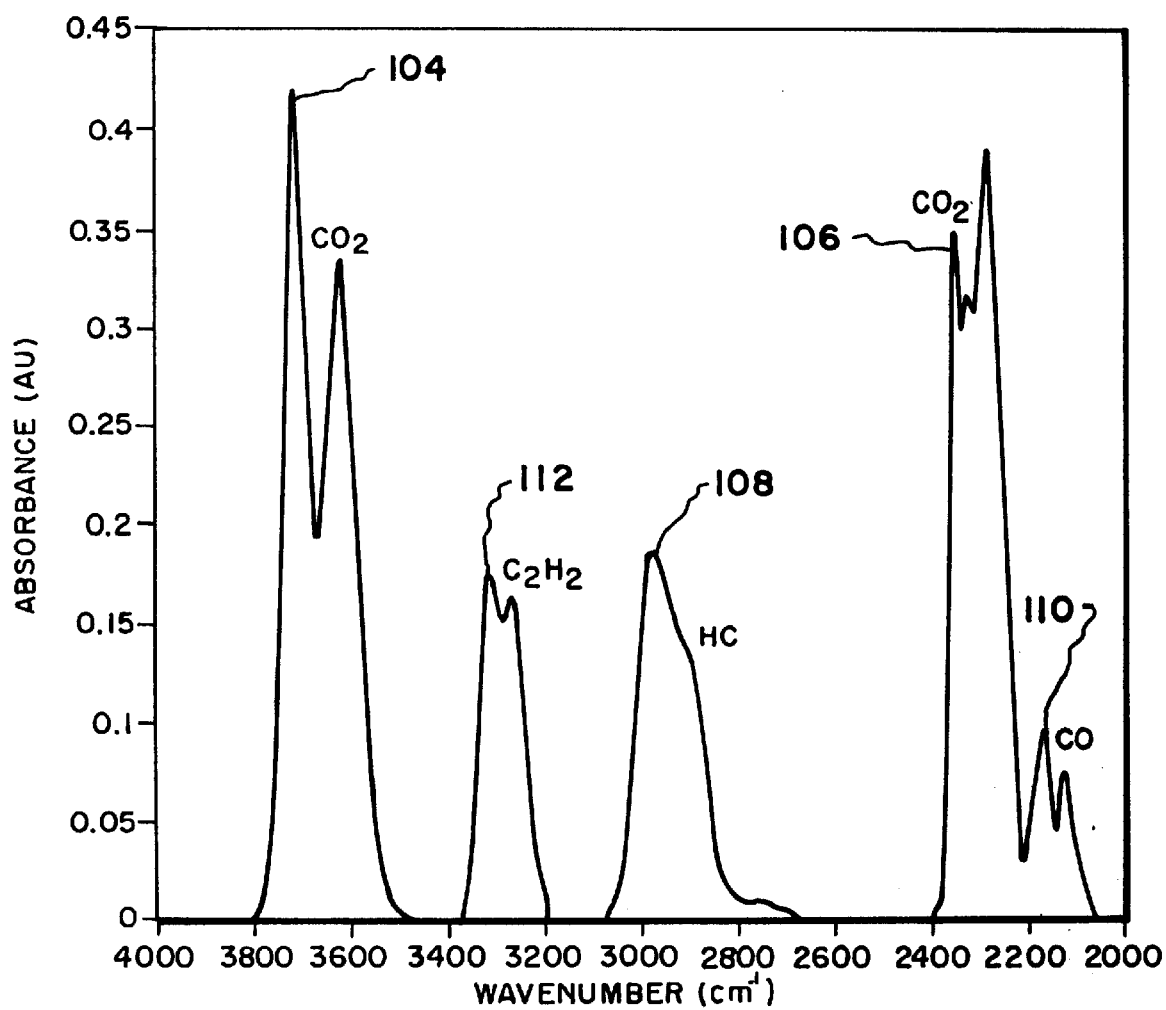
FIG. 7 is a graph illustrating the Mid-IR absorption bands of pollutants in vehicle exhaust emissions within a spectral range of IR spectrometer.

FIG. 7 is a graph of the Mid-IR absorption bands of pollutants in vehicle exhaust emissions within the spectral range of the IR spectrometer. $CO_2$ has two bands, 104 and 106, where-as HC (as propane), CO, and acetylene ($C_2H_2$) have one, 108, 110, and 112 respectively.

A Mid-IR absorption spectra, recorded with the disclosed invention, of analytes typically present in vehicle exhaust emissions is shown. Note that $CO_2$ has two peaks, 106, the fundamental asymmetric C=O stretch, and 104, a combination-overtone band. All other compounds HC (as propane), CO, and $C_2H_2$ only have one characteristic band, 108, 110, and 112 respectively, in the mid-IR. The spectra clearly illustrate how each of these important compounds can be detected in a mixture by virtue of their unique absorption signatures.

Figure 8:
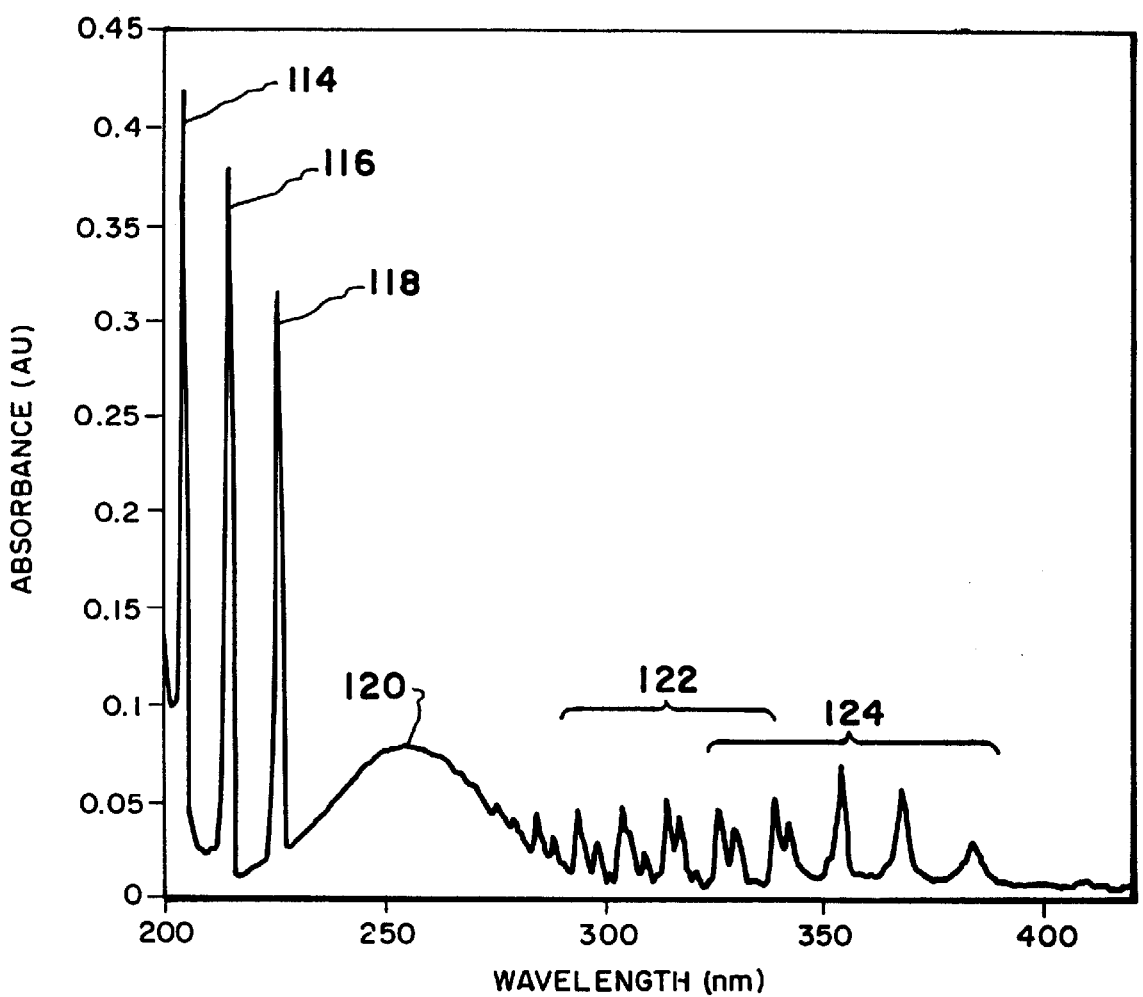
FIG. 8 is a graph illustrating the UV-vis absorption bands of pollutants in vehicle exhaust emissions within the spectral range of the UV spectrometer.

FIG. 8 is a graph of the UV-vis absorption bands of pollutants in vehicle exhaust emissions within the spectral range of the UV spectrometer. Bands 114, 116, and 118 correspond to NO, broad structure 120 corresponds to $O_3$ (not normally emitted directly in vehicle exhaust, but formed later photochemically), and peaks 122 and 124 correspond to HCHO and HONO respectively.

An analogous UV-vis spectrum of compounds found in vehicle exhaust emissions is shown. Three sharp, adjacent peaks at the short wavelengths 114, 116, and 118 are indicative of NO. Broad structure 120 is representative of $O_3$, and bands 122 and 124 result from the presence of HCHO and HONO, respectively.

Note that many more components of interest to remote sensing of vehicle exhaust emissions have characteristic absorption signatures in the spectral windows covered by FIGS. 7 and 8. For example, nitrous oxide, a potent greenhouse gas, is a strong absorber in the Mid-IR between CO and $CO_2$. Methane and methanol can also be measured between $C_2H_2$ and HC. In the UV-vis, $NH_3$, $NO_2$, $SO_2$, speciated aromatic hydrocarbons, phenol, benzaldehyde, HCHO and $CH_3CHO$ can also be conveniently measured with good sensitivity and selectivity. $SO_2$, an important atmospheric pollutant, is formed in significant amounts when the fuel has a high sulfur content. Diesel-powered vehicles often emit significant levels of $SO_2$, $NO_2$, aromatic hydrocarbons, and particulates. None of these emissions can be monitored with previously patented inventions.

The graphs of FIGS. 5 through 8 illustrate a key aspect of the disclosed invention: using coupled mid-IR and UV-vis spectrometers to generate wavelength-resolved data on the monitored exhaust plume, where "wavelength-resolved" means a spectrum consisting of 64 pixels, or more. The use of this wavelength-resolved UV-vis-IR data to optically probe vehicle exhaust emissions in a remote sensing configuration is unique to the invention. The inventions described in the patents of Bishop et al., Jack et al., Sullivan et al., and Swanson, Jr. all share several common features that differ from the present invention, as described below.

In relevant, preceding inventions, each IR absorber (i.e., CO, $CO_2$, HC, and sometimes NO and $H_2O$) is measured by a separate "channel". This channel consists of a dedicated detector, usually a lead selenide photodetector and the desired spectral window is isolated by the corresponding narrow bandpass optical filter. When the above five gases are measured in the IR, five or six (i.e., five samples and a reference) detectors need to be used. Adding more measurement channels (e.g., $N_2O$) means that an additional detector, optical filter, and pre-amp PCB needs to be added. In practice, this means that these inventions are limited to the above five gases.

The use of multiple detectors in the above fashion also means that light has to be channeled to all of them sequentially (e.g., rotating polygonal mirror described by Bishop et al. or the rotating filter wheel described by Swanson, Jr.) or simultaneously (e.g., multiple detectors on a single substrate in conjunction with a beam homogenizer described by Jack et al.). This complicates the optical design and often makes it less robust and more difficult to align than a single spectrometer, such as in the present invention.

When a UV signal is employed in tandem with the IR signal, the Bishop et al. and Sullivan et al. patents describe a means of combining the UV and IR beams and making them coaxial. The combined beams are separated once they have crossed the roadway by a similar means. Such a means consists of a dichroic beam splitter, an optical device that transmits IR radiation and reflects UV radiation, or vice versa. For the device to have the required broad spectral window in the Mid-IR to measure HC, CO, and $CO_2$ (i.e., $\approx 1,100$ cm$^{-1}$) as shown in FIG. 7, it can only have a very narrow spectral range in the UV (maximum $\approx 10$ nm). This is an unavoidable result of optical coating technology. This arrangement means that only peak 118, for example, is available for NO monitoring in the UV. In other words, only a maximum of 10 nm are available anywhere in the spectral bandwidth of the spectrometer, which could be as high as 200 nm. This results in very inefficient usage of the UV spectrometer (≈5%) and generally means that only a narrow band from one single compound, typically NO peak 118, can be monitored. The remaining information is lost. This rationale also applies to the invention described in the patent of Bishop et al., the only case where a dispersive UV spectrometer is used as part of a patented vehicle exhaust remote sensor.

In the present invention, the IR and UV beams are slightly offset and, thus, do not require separation by an optical device, such as a dichroic beam splitter. Therefore, a broad spectral window can be monitored in the UV-vis and in the IR simultaneously. This dramatically increases the usefulness of the invention as numerous compounds can be monitored simultaneously in addition to the usual molecules, CO, $CO_2$, HC, and NO, without the need for more hardware. For instance, dust can be measured in the visible portion of the electromagnetic spectrum with the same spectrometer that measures NO; numerous additional analytes can also be added in the UV and IR (see above).

In preceding inventions relating the remote sensing of vehicle exhaust emissions (see above), attenuation of the signal, generated from the response of the photodetector to the radiation isolated by a narrow bandpass optical filter, is directly related to the corresponding gas concentration. Rather than observing an absorption pattern (i.e., two dimensional signal shown in FIGS. 7 and 8), as with the present invention, these detectors output a voltage (i.e., a one dimensional signal) that is amplified and processed in the electronics. Therefore, no chemometric analysis on the gas absorption data is possible, thereby limiting the sensitivity and selectivity of the measurement. Turbulence and particles in the exhaust plume, for instance, may yield artificial signals. This does not happen in the present invention as both spectrometers yield wavelength-resolved spectral data that can be processed mathematically as detailed below.

Figure 9A:
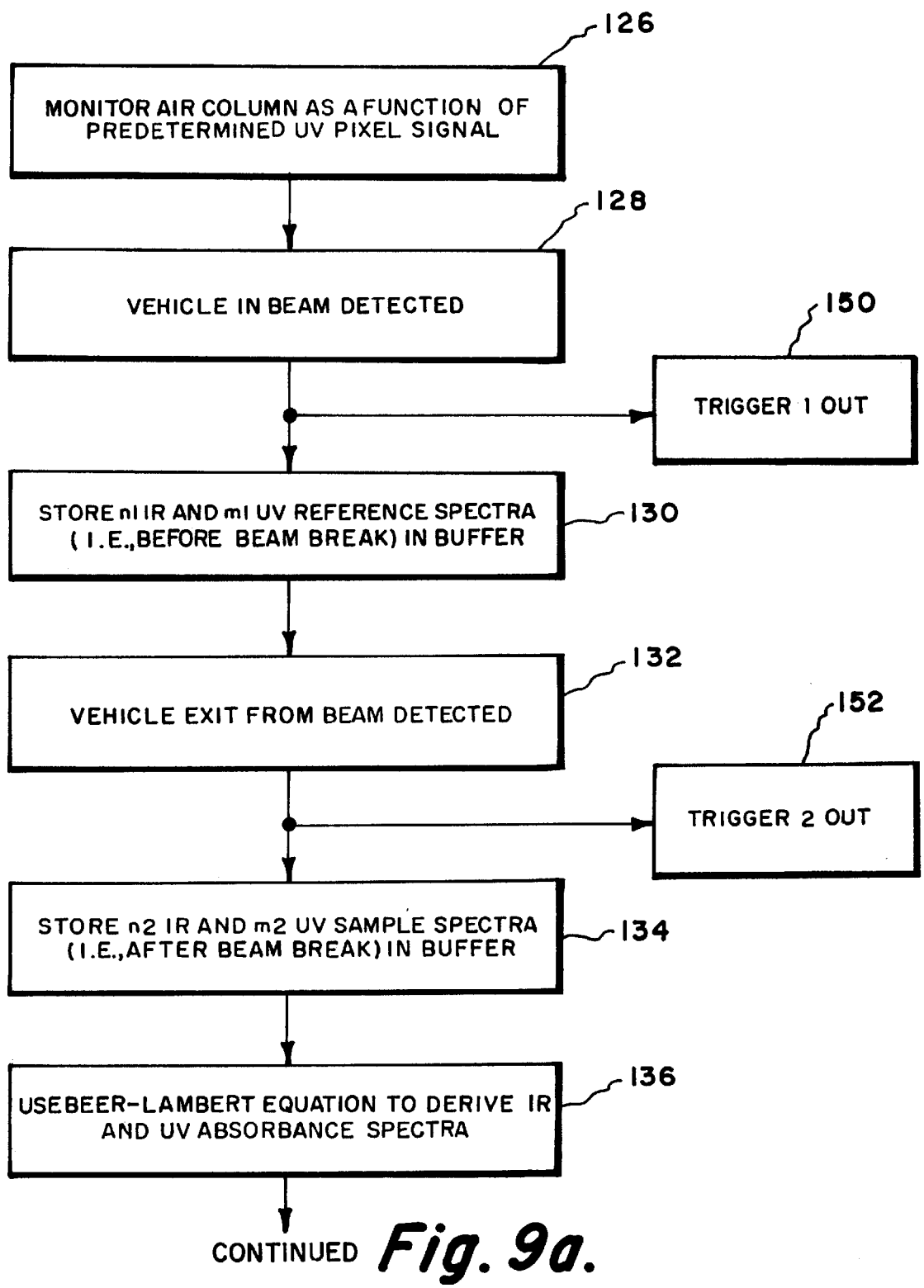
FIG. 9 is a flow diagram illustrating the chain of events that takes place with the synchronized IR and UV-vis digital data to analyze, display, and calculate gas and dust concentrations respectively.
Figure 9B:
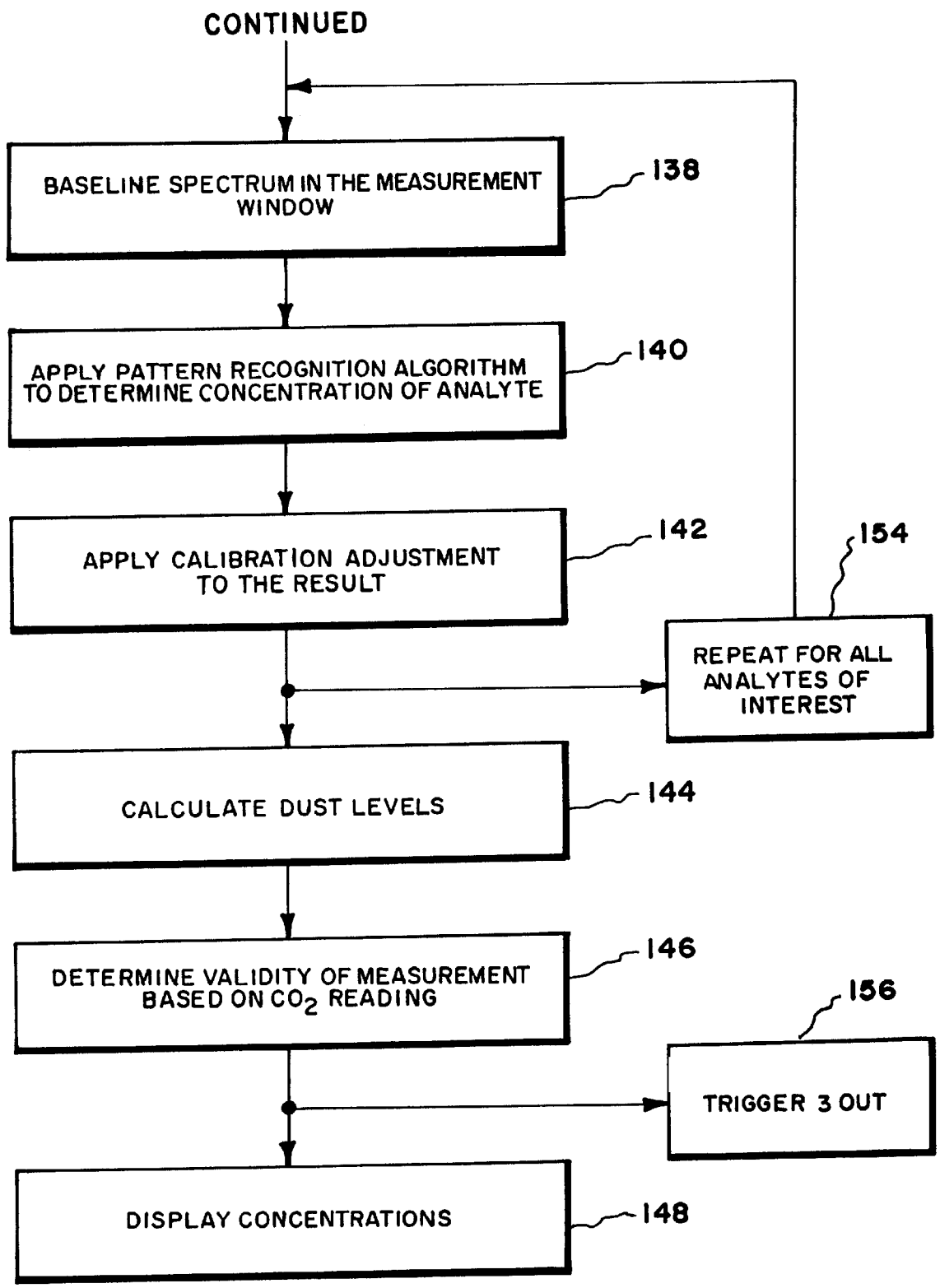

FIG. 9 is a flow diagram of the chain of events that takes place with the synchronized IR and UV-vis digital data to afford gas and dust concentrations and shows how these measurements are preformed in the disclosed invention. First, "dark" IR and UV spectra are collected, typically once to 5 times daily, during the course of field measurements with the beams blocked. These spectra are stored in the analyzer. The optically aligned analyzer monitors the air column 126 defined by the pairs of IR and UV beams traversing the roadway. A predetermined, user-selectable UV pixel, measuring a wavelength where no components of vehicle exhaust typically absorb radiation, is used to determine if a vehicle, or other object or body, blocks the optical probe. This is typically carried out at a high frequency, such as 100 Hz. Once a vehicle is detected (128), trigger signal 150 is output from the analyzer. This can be used to synchronize the instrument readings with peripheral equipment such as the license plate reader and the speed/acceleration monitor.

Multiple reference spectra, corresponding to the optical transmission of the air column across the roadway just prior to entry by the vehicle, and multiple measurement spectra, corresponding to the optical transmission of the air column across the roadway just following the vehicle, are recorded. Reference spectra are stored in rotating buffer 130. Once the instrument has validated the vehicle's emergence from the optical beams 132, using the same approach used to determine when the vehicle enters the beams, trigger signal 152 is output from the analyzer. Sample spectra are stored in binary files 134, along with the corresponding reference spectra and are either processed in real time or saved for post processing. Note that each spectrum in a set of measurement spectra can be accessed independently during post-processing, allowing the profile of the exhaust plume to be studied. When two cars are close together, one set of sample spectra may become the next car's reference spectra. To achieve a smooth "recycling" of these readings n2 and m2 are usually one reading or more greater than n1 and m1.

The Beer-Lambert law is applied 136 to the corresponding "dark" (drk), reference ($I_0$), and sample (I) spectra to generate absorbance spectra, (A):

$$A = \log_{10}[(I_0 - drk)/(I - drk)] = \epsilon c x l$$

Where, $\epsilon$ is the molecular extinction coefficient of the analyte, c is the concentration of the analyte, l is the optical pathlength.

Note that the optical pathlength used for instrument calibration typically corresponds to the average tailpipe diameter (≈4.5 cm) times the number of optical passes.

Typical absorbance spectra of vehicle exhaust components are shown in FIGS. 7 and 8. Using the above approach insures that the sample spectra are representative only of the exhaust plume, as any background effects are present in both I and I0 and, thus, cancel out. This procedure can either be applied in real time, or post-processing mode.

The speed of modern-day PCs allows sophisticated signal processing on this spectral data to be applied in real time. First, the absorbance spectrum is linearly baselined 138 over the wavelength range corresponding to the absorption band of the analyte being measured. Multi-point, higher order polynomials can also be used for baselining when required. This eliminates any skewing or shifting of the spectrum due to scattering. Next, a pattern recognition algorithm 140 is applied to this data, using a spectrum of the measured analyte from a spectral database as a reference pattern. Mathematical approaches to pattern recognition 140 include partial and classical least squares fits, using the singular value decomposition theorem and/or neural networks. The latter is usually only used for post-processing. This chemometric treatment of the data allows characteristic structures to be extracted from a very low signal-to-noise ratio, sometimes below unity.

The pattern recognition fit result is then filtered through a polynomial calibration adjustment curve 142 determined experimentally in the laboratory with certified cylinder gases flowed through an in-line calibration cell between the corresponding radiative source and spectrometer. This linearization compensates for deviations from ideal Beer-Lambert behavior. The above signal processing is repeated 154 for all analytes of interest.

Dust levels are calculated 144 from the baselined attenuation of a signal in the visible portion of the electromagnetic spectrum, such as deuterium emission line 102 (FIG. 6). Attenuation of the signal due to scattering can also be monitored at a plurality of wavelengths, where typical vehicle exhaust components are known not to absorb. This way, scattering as a function of radiation wavelength can be measured yielding additional information on the particulates in the beam (e.g., size distribution).

The validity of the above measurements can conveniently be assessed based on the measured $CO_2$ concentration. Most vehicles emit a predictable amount of $CO_2$, as a result of stoichiometric fuel combustion. If the measured concentrations are well below this expected value, poor beam overlap with the plume was probably achieved, or the volume of exhaust emitted by the vehicle was low (e.g., during idle). This criterion is used to determine the validity of measurement 146 and accept or reject the data set. When data has been validated, trigger signal 156 is output and the concentrations are displayed 148 and transmitted in digital form to the operator PC. Note that the concentration of these species can be displayed in a variety of ways, including "raw" (i.e., as measured in the diluted plume), rationed to $CO_2$ levels, and regressed to levels in undiluted exhaust. The latter is achieved using combustion thermodynamics to estimate the actual $CO_2$ emissions based on $CO/CO_2$ and $HC/CO_2$ ratios (i.e., calculating the carbon balance). Once the actual, undiluted $CO_2$ concentration has been calculated, the remaining readings can be normalized for dilution and optical plume overlap.

The present invention is not limited in its usefulness to vehicle exhaust emission monitoring. Other applications include:

Remote sensing of exhaust emissions from stationary or moving heavy duty vehicles (i.e., trucks with a raised exhaust stack), airplanes, boats, or any other motor-driven vessel, vehicle, or craft, Open path monitoring of an air column. This measurement could either monitor very fast processes (i.e., in the order of msec.) or slow variations (e.g., diurnal fluxes). Applications include:
Tunnel monitoring,
Ambient air quality monitoring,
Monitoring of ambient fluxes in precision agriculture where fertilizer and pesticide application dosage is targeted according to need,
Perimeter monitoring and leak detection,
Flame spectroscopy (e.g., combustion monitoring) and other pilot scale research, where the process under investigation is located between the analyzer and the return optics, Imaging of gas plumes (e.g., forest fires, volcanoes, stationary sources), Open path monitoring where the distance between the analyzer and the return optics is increased form several meters to longer distances, up to several kilometers. The optically probed air column would be monitored for small ($\approx$low ppb) variations in ambient concentrations of trace gases.

This invention is not to be limited by the embodiment shown in the drawings and described in the description which is given by way of example and not of limitation, but only in accordance with the scope of the appended claims.

What is claimed is:

1. A vehicle exhaust emission monitoring system comprising;
    an IR radiation source;
    a collimating optical system for collimating IR radiation from said IR source;
    a UV radiation source;
    a collimating optical system for collimating UV radiation from said UV source;
    said IR radiation and UV radiation being physically spatially offset at the source;
    a reflector mirror assembly on the opposite side of a path of travel of said vehicle from said IR and UV radiation; said IR and UV radiation converging at said reflector mirror so that said IR and UV radiation makes multiple passes across said path;
    optical assemblies receiving and calibrating said IR and UV radiation respectively;
    IR and UV spectrometers receiving said IR and UV radiation respectively from said optical assemblies for generating wavelength resolved spectra; and
    processing means for processing said wavelength resolved spectra from said IR and UV spectrometers to detect and measure an analyte of interest;
    whereby a plurality of analytes can be detected and analyzed.

2. The system according to claim 1 in which said reflector mirror assembly includes;
    a single spherical mirror on the opposite side of said path receiving said IR and UV radiation whereby said IR and UV radiation makes two passes across said path.

3. The system according to claim 2 in which said single spherical mirror comprises; a single spherical mirror with adjustable and variable focal length on the opposite side of said path receiving said IR and UV radiation whereby said IR and UV radiation makes two passes across said path.

4. The system according to claim 1 in which said reflector mirror assembly includes;
    a pair of reflector mirrors on the opposite side of said path and a third reflector mirror on the same side of said IR and UV sources receiving said IR and UV radiation whereby said IR and UV radiation makes two or more passes across said path.

5. The system according to claim 4 in which said reflecting mirrors are spherical mirrors.

6. The system according to claim 5 in which said optical assembly for receiving said IR and UV radiation comprise a sealed optical calibrating assembly for calibration and projecting said IR and UV radiation on an entrance slit of said respective spectrometer.

7. The system according to claim 5 in which said optical assembly includes a pair of Schwarzshield telescopes for each of said IR and UV radiation beams.

8. The system according to claim 4 in which said IR and UV spectrometers comprise; a rapid scanning detector device having a grating mounted in a synchronous motor.

9. The system according to claim 8 in which said rapid scanning detector device is a plurality of rapid scanning detector devices.

10. The system according to claim 8 in which said IR and UV spectrometers comprise an FTIR and FTUV spectrometer respectively.

11. The system according to claim 4 in which said IR and UV spectrometers comprise a detector array.

12. The system according to claim 11 in which said detector array comprises at least 128 detectors optically interfaced to a grating.

13. The system according to claim 11 in which said detector array comprises a 2-D detector array comprised of at least 16×16 pixels, interfaced to an optical means for separating broadband radiation into component wavelengths.

14. The system according to claim 1 in which said processing means comprises a PC, said PC applying the Beer-Lambert law to collected and stored dark spectra and sample spectra to provide an absorbance spectrum of a vehicle exhaust plume.

15. The system according to claim 1 in which said processing means comprises a PC, said PC processing the collected spectral data to linearly baseline the wavelength range corresponding to the absorption band of the analyte being measured; and applying a pattern recognition algorithm to the spectral data using a spectrum of the measured analyte from a spectral database as a reference pattern.

16. The system according to claim 15 in which said algorithms include a singular value decomposition theorem and/or a neural network.

17. A method of monitoring vehicle exhaust emissions comprising;

projecting an IR beam from a source;

collimating said IR beam;

projecting a UV beam from a source;

collimating said UV beam;

spatially offsetting said IR beam and said UV beam from their source;

reflecting said IR beam and said UV beam from a mirror on an opposite side of the path of travel off said vehicle from said IR and UV sources, said IR beam and UV beam converging at said mirror so that said IR beam and UV beam make more than one pass across the path of said vehicle;

calibrating radiation received from said IR beam and UV beam with an optical assembly;

generating wavelength resolved spectra by IR and UV spectrometers from radiation received from said IR beam and UV beam;

processing said wavelength resolved spectra from said IR and UV spectrometers to measure an analyte of interest;

whereby a plurality of analytes can be detected and analyzed.

18. The system according to claim 17 including reflecting said IR beam and UV beam from a plurality of mirrors on the opposite side of said path of said vehicle and a reflective mirror on the same side as said IR and UV sources to produce two or more passes across said path.

19. The system according to claim 18 including calibrating said IR and UV radiation in optical assemblies that comprise sealed in-line calibration cells.

20. The system according to claim 17 in which said wavelength resolved spectra is generated by IR and UV-vis spectrometers.

21. The system according to claim 20 in which said processing comprises;

applying Beer-Lambert law to stored dark IR and UV spectra collected and sample spectra to provide an absorbance spectrum of said vehicle exhaust plume.

22. The system according to claim 20 in which said processing comprises;

applying a pattern recognition algorithm to an absorbance spectrum using a reference spectral database.

23. The system according to claim 22 in which said algorithm comprises; applying a singular valve decomposition theorem and/or a neural network.

24. The system according to claim 20 in which said processing mans comprises; linearly baselining an absorbance spectrum over the spectral range corresponding to an absorption pattern of an analyte of interest.

* * * * *